(12) United States Patent
Miura et al.

(10) Patent No.: US 6,528,658 B1
(45) Date of Patent: Mar. 4, 2003

(54) PROCESS FOR PREPARING CYCLOALKANONE

(75) Inventors: Hiroyuki Miura, Takasago (JP); Hitoshi Watanabe, Himeji (JP); Tomohide Ina, Himeji (JP); Hidehiko Nakajima, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/673,568
(22) PCT Filed: Feb. 8, 2000
(86) PCT No.: PCT/JP00/00690
§ 371 (c)(1), (2), (4) Date: Oct. 18, 2000
(87) PCT Pub. No.: WO00/48975
PCT Pub. Date: Aug. 24, 2000

(30) Foreign Application Priority Data

Feb. 19, 1999 (JP) ............................. 11-042106

(51) Int. Cl.$^7$ ..................... C07D 209/02; C07D 207/02
(52) U.S. Cl. ..................... 548/466; 548/486; 548/542
(58) Field of Search ................... 548/466, 486, 548/542

(56) References Cited

FOREIGN PATENT DOCUMENTS

| EP | 0 450 498 A1 | 10/1991 |
|---|---|---|
| EP | 0858835 | * 2/1998 |
| EP | A1824962 | 2/1998 |
| EP | A1864555 | 9/1998 |
| JP | A927215 | 3/1998 |

\* cited by examiner

*Primary Examiner*—Cecilia Tsang
*Assistant Examiner*—Andrea D. Small
(74) *Attorney, Agent, or Firm*—Birch, Stewart, Kolasch & Birch, LLP

(57) ABSTRACT

A series of steps of (A) a step for bringing a cycloalkane into contact with molecular oxygen (oxidizing reactor 2) in the presence of an oxidizing catalyst having an imide unit of the following formula (I):

wherein X represents oxygen atom or hydroxyl group;
(B) a step for separating the catalyst, and by-produced acid component or a derivative thereof from the reaction mixture (filter 3, extracting column 4, hydrolyzing unit 7, saponifying unit 8); and
(C) steps for separating the cycloalkane, a cycloalkanol, and a cycloalkanone from the reaction mixture individually (distilling columns 5, 6, 9, and 10) makes it possible to produce cycloalkanones efficiently. A first component (lower-boiling point component) containing the cycloalkane and a second component (higher-boiling point component) containing the cycloalkanone and cycloalkanol may be separated from the reaction mixture, and the cycloalkanone and the cycloalkanol may be separated from the higher-boiling point component. Such production process is capable of providing cycloalkanones with high efficiency.

19 Claims, 4 Drawing Sheets

PROCESS FOR PREPARING CYCLOALKANONE

This application is the national phase under 35 U.S.C. §371 of PCT International Application No. PCT/JP00/00690 which has an International filing date of Feb. 8, 2000, which designated the United States of America.

TECHNICAL FIELD

The present invention relates to a process for producing a cycloalkanone from a cycloalkane using molecular oxygen in the presence of a particular oxidizing catalyst.

BACKGROUND TECHNOLOGY

Among cycloalkanones, cyclohexanone is a compound useful in producing ε-aminocaprolactam which is a raw material for nylon. It is known that, in the production of cyclohexanone, in the liquid phase, cyclohexane is oxidized with molecular oxygen or a molecular oxygen-containing gas in the presence of a soluble cobalt salt as a catalyst (e.g., cobalt 0.1 to 100 ppm) to form cyclohexanone and cyclohexanol, followed by the conversion of the by-produced cyclohexanol into a cyclohexanone by subjecting the cyclohexanol to a dehydrogenating reaction using a dehydrogenator ("Handbook of Chemistry: Applied Chemistry" page 536, Oct. 15, 1986 version, edit by Nippon Kagaku-kai, published by Maruzen).

However, a conventional process not only involves the generation of a large amount of by-products but also pose a problem of low production rate of cyclohexanone, and further requires the by-produced cyclohexanol be treated by dehydrogenation. Moreover, when nitric acid or the like is employed for the oxidation of a cycloalkane, the process requires the use of an expensive exhaust gas-treatment facilities. Therefore, despite the process being complicated, a cyclohexanone cannot be obtained with high efficiency.

Thus, an object of the present invention is to provide a process capable of producing cycloalkanones high production rates through a sequence of steps.

Another object of the present invention is to provide a process capable of efficiently producing cycloalkanones through a sequence steps without subjecting a by-produced cycloalkanol to a dehydrogenating step.

Still another object of the present invention is to provide a process capable of producing, under mild or moderate conditions, cycloalkanonesat high conversions and selectivities without requiring the treatment of exhaust gas.

DISCLOSURE OF THE INVENTION

The inventors of the present invention made intensive and extensive studies to achieve the above objects, and finally found that a cycloalkanone can be efficiently formed by oxidizing a cycloalkane in the presence of a specific oxidizing catalyst (oxidation catalyst) through a series of steps. The present invention was accomplished based on the above findings.

That is, the present invention is a process for producing cycloalkanones from cycloalkanes using an oxidizing catalyst having an imide unit represented by the following formula (I):

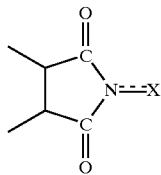

(I)

wherein X represents oxygen atom or hydroxyl group,
which comprises (A) a step for bringing a cycloalkane into contact with molecular oxygen in the presence of the aforementioned oxidizing catalyst, (B) a step (s) for separating the catalyst, and a by-produced acid component or a derivative thereof from the reaction mixture, and (C) steps for separating the cycloalkane, a cycloalkanol, and a cycloalkanone from the reaction mixture.

Further, from the reaction mixture may be separated a lower-boiling point component comprised of the cycloalkane, and a higher-boiling point component comprised of the cycloalkanone and the cycloalkanol. The cycloalkanone and cycloalkanol may be separated from the higher-boiling point component, and the cycloalkane and lower-boiling point impurities may further be separated from the lower-boiling point component. Further, the cycloalkanone, cycloalkanol, and higher-boiling point impurities may be separated from the higher-boiling point component. The acid component or a derivative thereof may be separated by extraction, hydrolysis, saponification, or neutralization. The cycloalkanone and the cycloalkanol, and the acid component or derivative thereof treated by means of extraction, hydrolysis, saponification or netralization may be separated from the reaction mixture individually. The reaction can be effected in the presence of a solvent, and in that case, the solvent may be separated from the reaction mixture.

The process of the present invention may comprise (A) the oxidation step, (i) a step for separating a lower-boiling point component, a higher-boiling point component, and a component containing the oxidizing catalyst, a by-produced acid component, and a derivative of the acid component by distillation; (ii) a step for separating the cycloalkane from the lower-boiling point component and then recycling the separated cycloalkane to the oxidizing reaction system; and (iii) a step for separating the cycloalkanol from the higher-boiling point component and then recycling the separated cycloalkanol to the oxidizing reaction system. The oxidizing catalyst may be separated from the component containing the oxidizing catalyst, the by-produced acid component and a derivative thereof and then recycled to the oxidizing reaction system. There is the option of carrying out the reaction in the presence of a solvent. In that case, the solvent may be separated from the reaction mixture and recycled to the oxidizing reaction system. By-produced water may be separated from the lower-boiling point component, with which water the acid component or a derivative thereof may be treated by at least one means selected from extraction, hydrolysis, saponification, and neutralization. These steps may be carried out continuously.

As the cycloalkane, a $C_{4-10}$cyclohexane (particularly, cyclohexane) can be used, and the oxidizing catalyst may be used together with a co-oxidizing agent.

BEST MODE FOR CARRYING OUT THE INVENTION

Hereinafter, the present invention will be described in further detail with reference to the attached drawings, if necessary.

The process of the present invention need only comprise (A) an oxidation step, (B) a step(s) for separating a catalyst, and an acid component which is by-produced or a derivative thereof from the reaction mixture, and (C) steps for separating a cycloalkane, a cycloalkanol, and a cycloalkanone from the reaction mixture.

Figure 1:
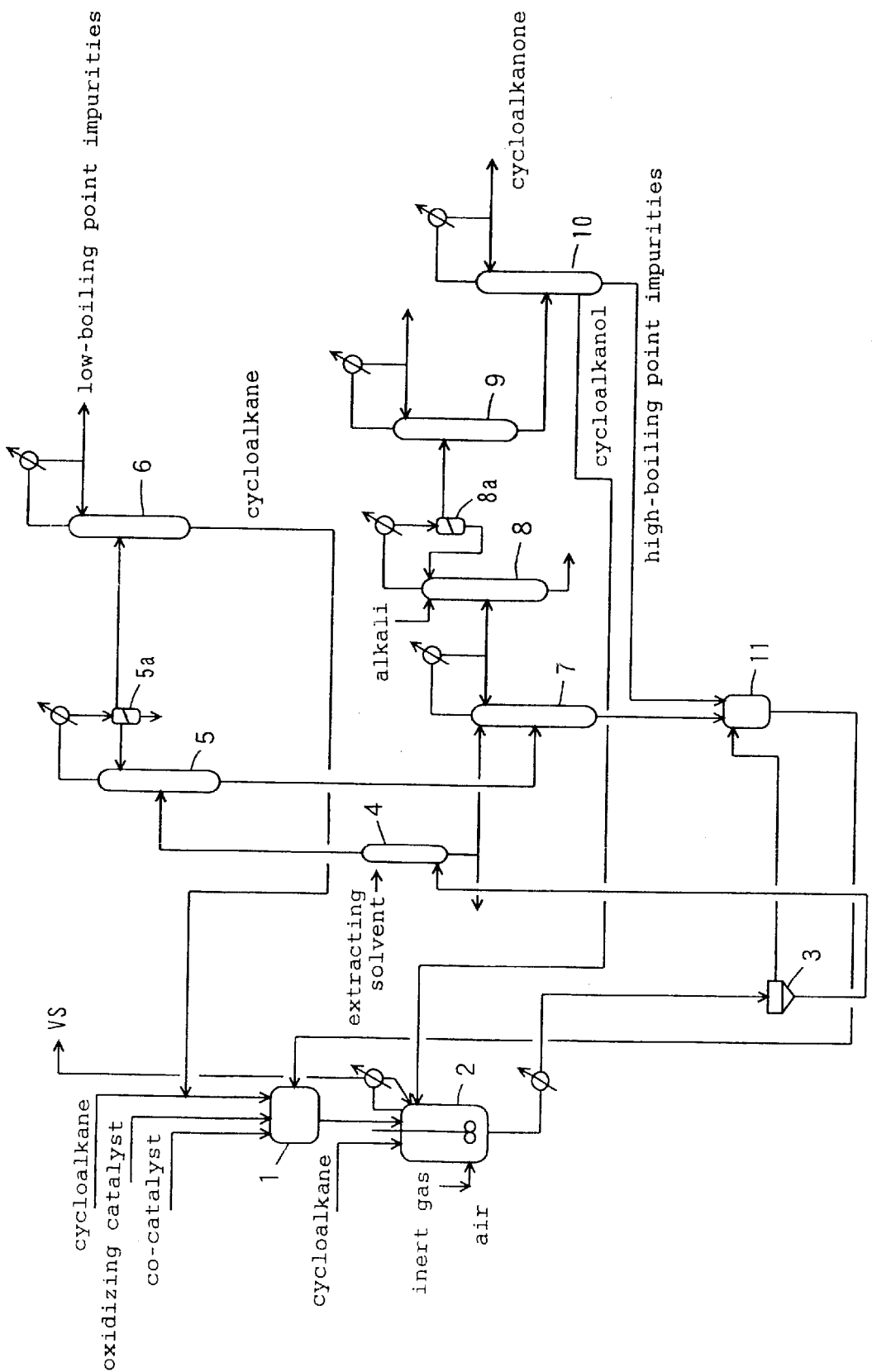
FIG. 1 is a flow-chart for explaining the process of the present invention.

FIG. 1 is a flow chart for explaining the production process of the present invention. In this embodiment, there are a step for preparing a catalytic solution containing a compound having an imide unit of the formula (I) (hereinafter, sometimes referred to simply as an imide compound) in a mixing vessel 1, (A) a step for forming a cycloalkanone using the catalytic solution by bringing a cycloalkane into contact with molecular oxygen in an oxidizing reactor 2, (B1) a step for separating the catalyst from the obtained reaction mixture, (B2) a step for separating an acid component from the reaction mixture, (C1) a step for separating a lower-boiling component from the reaction mixture from which the catalyst and the acid component have been separated (B3) a step for separating impurities such as a carboxylate from the reaction mixture from which a lower-boiling point component such as the cycloalkane or water has been separated, and (C2) a step for separating a higher-boiling component from the reaction mixture from which the lower-boiling component(s) and impurities have been separated. In the separation step (C2) for separating the higher-boiling point component, the cycloalkanone and a cycloalkanol have been separated. Moreover, the separation step (B) is constituted of (B1) a step for separating the catalyst from the reaction mixture, (B2) a step for separating the acid component, and (B3) a step for separating impurities such as a carboxylate from the reaction mixture, and the separation step (C) is constituted of (C1) a step for separating the lower-boiling point component from the reaction mixture and (C2) a step for separating the higher-boiling point component from the reaction mixture. Incidentally, the oxidizing reaction may be effected by reactive distillation, for example, by distilling water and the cycloalkane by azeotropy and totally ref luxing the cycloalkane phase while extracting the aqueous phase. Moreover, the cycloalkane, cycloalkanol, and the catalyst separated from the reaction mixture may be recycled to the mixing vessel 1 or the reactor 2.

(Oxidizing Catalyst)

As the oxidizing catalyst which catalyzes the oxidation of the cycloalkane with molecular oxygen, use can be made of a compound having an imide unit represented by the formula (I):

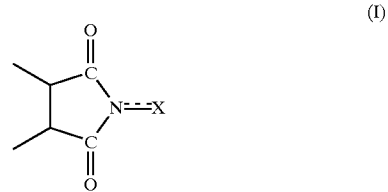

wherein X stands for oxygen atom or hydroxyl group.

The preferable oxidizing catalyst is a compound of the following formula (II):

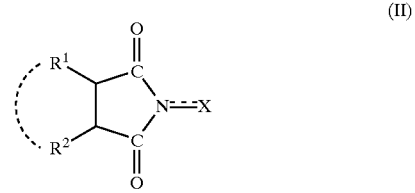

wherein $R^1$ and $R^2$ are the same or different, each representing a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may coupled together to form a double bond or an aromatic- or non-aromatic ring; the aromatic- or non-aromatic ring composed of $R^1$ and $R^2$ may have at least one imide unit represented by the aforementioned formula (I); and X has the same meaning as defined above.

In a compound of the formula (II), examples of the halogen atom designated by the substituent $R^1$ or $R^2$ include iodine, bromine, chlorine, and fluorine. Alkyl groups include, e.g., straight- or branched-chain alkyl groups having about 1 to 10 carbon atoms such as methyl, ethyl, propyl, isopropyl, butyl, isobutyl, sec-butyl, t-butyl, pentyl, hexyl, heptyl, octyl, and decyl (preferably, $C_{1-6}$ alkyl groups, particularly $C_{1-4}$ alkyl groups).

Aryl groups include phenyl group and naphtyl group, and cycloalkyl groups include $C_{3-10}$ cycloalkyl groups such as cyclopentyl, cyclohexyl, and cyclooctyl groups. Alkoxy groups include alkoxy groups having about 1 to 10 carbon atoms, such as methoxy, ethoxy, propoxy, isopropoxy, butoxy, isobutoxy, t-butoxy, pentyloxy, and hexyloxy, preferably $C_{1-6}$ alkoxy groups, and particularly $C_{1-4}$ alkoxy groups.

Alkoxycarbonyl groups include alkoxycarbonyl groups having about 1 to 10 carbons atoms in an alkoxy moiety (preferably, $C_{1-6}$alkoxy-carbonyl groups, $C_{1-4}$alkoxy-carbonyl groups), such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, and hexyloxycarbonyl group.

As the acyl group, there may be exemplified those having about 1 to 6 carbon atoms, such as formyl, acetyl, propionyl, butyryl, isobutyryl, valeryl, isovaleryl, and pivaloyl groups.

The substituents $R^1$ and $R^2$ may be the same or different. Moreover, in the formula (II), the substituents $R^1$ and $R^2$ may bond together to form a double bond or an aromatic- or non-aromatic ring. Preferred aromatic- or non-aromatic rings are about 5 to 12-membered ones, particularly about 6 to 10-membered ones. The ring may be a heterocycle or a condensed heterocycle, though a hydrocarbon ring in many cases. The aromatic- or non-aromatic ring may have at least one imide unit represented by the formula (I) (usually, one or two imide units). Examples of such ring include non-aromatic alicyclic rings (e.g., cycloalkane rings which may have a substituent, such as cyclohexane ring; cycloalkene rings which may have a substituent, such as cyclohexene ring); non-aromatic bridged rings (e.g., bridged hydrocarbon rings which may have a substituent, such as 5-norbornene ring); and aromatic rings which may have a substituent, such as benzene ring and naphthalene ring. In many instances, the aforementioned ring is constituted of an aromatic ring.

Included among the preferred imide compounds are compounds expressed by the following formula:

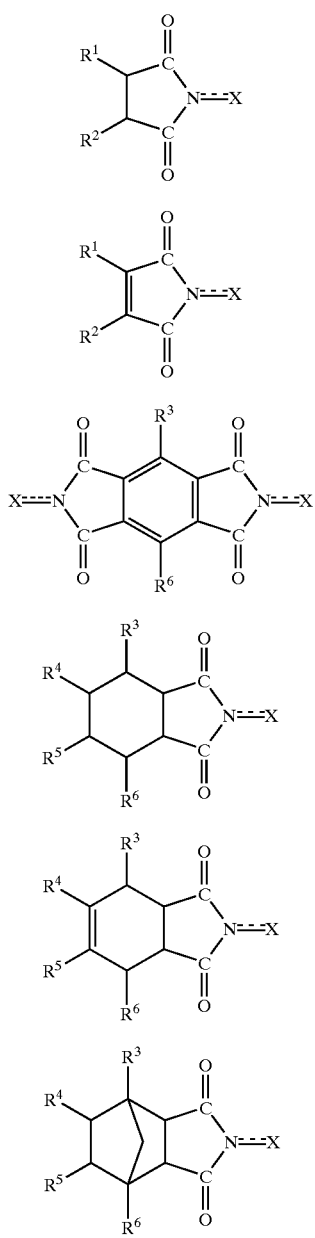

wherein $R^3$ to $R^6$ are the same or different, each representing a hydrogen atom, an alkyl group, a hydroxyl group, an alkoxy group, a carboxyl group, an alkoxycarbonyl group, an acyl group, a nitro group, a cyano group, an amino group, or a halogen atom; and $R^1$, $R^2$, and X have the same meanings as defined above.

As to the substituents $R^3$ to $R^6$, examples of the alkyl group, alkoxyl group, alkoxycarbonyl group, acyl group, and halogen group are similar to those listed above. Usually, the substituents $R^3$ to $R^6$ each stands for, in many instances, a hydrogen atom, a lower alkyl group having about 1 to 4 carbon atoms, a carboxyl group, a nitro group, or a halogen atom.

Imide compounds of the formula (I) can be used either singly or as a combination of two or more.

Acid anhydrides corresponding to the imide compounds represented by the formula (I) include saturated or unsaturated aliphatic dicarboxylic acid anhydrides such as succinic anhydride and maleic anhydride; saturated or unsaturated non-aromatic cyclic polycarboxylic acid anhydrides (alicyclic polycarboxylic acid anhydrides) such as tetrahydrophthalic acid anhydride, hexahydrophthalic acid anhydrides (1,2-cyclohexane dicarboxylic acid anhydride), 1,2-anhydride of 1,2,3,4-cyclohexanetetracarboxylic acid; bridged cyclic polycarboxylic acid anhydrides (alicyclic polycarboxylic acid anhydrides) such as hetic acid anhydride and himic acid anhydride; and aromatic polycarboxylic acid anhydrides such as phthalic anhydride, tetrabromophthalic anhydride, tetrachlorophthalic anhydride, nitrophthalic anhydride, trimellitic anhydride, methylcyclohexene tricarboxylic acid anhydride, pyrromellitic anhydride, mellitic anhydride, and 1,8;4,5-naphthalenetetracarboxylic acid dianhydrides.

Examples of the preferrred imide compound include N-hydroxysuccinimide, N-hydroxymaleimide, N-hydroxyhexa-hydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide. A particularly preferred compound includes an N-hydroxyimide compound derived from an alicyclic polycarboxylic anhydride, especially one derived from an aromatic polycarboxylic anhydride, such as N-hydroxyphthalimide.

[Production Step of Oxidizing Catalyst]

The imide compound can be prepared through a conventional imidation reaction, for example, by reacting the corresponding acid anhydride with hydroxylamine $NH_2OH$ to open the ring of the acid anhydride group and then closing the ring for imidation. To be more concrete, when the oxidizing catalyst is N-hydroxyphthalimide, with phthalic anhydride and hydroxylamine as raw materials for the catalyst, the oxidizing catalyst may be prepared by reactively distilling the reaction mixture while removing water generated in the reaction. The oxidizing catalyst can be produced in a conventional manner, such as in a batch system, a semi-batch system, or a continuous system.

The oxidizing catalyst thus obtained can be subjected, as it is, to a catalytic solution-preparing step which will be described later. Incidentally, as will be explained hereinafter, the oxidizing catalyst or the co-oxidizing agent may be separated from the reaction mixture, regenerated, and recycled to the reaction system, if desired.

[Production Step of Hydroxylamine]

For example, hydroxylamine as a raw material for the oxidizing catalyst can be prepared in the following manner.

Ammonia (this may be ammonia which is by-produced in a catalyst-regenerating step which will be described later) is oxidized with molecular oxygen thereby to form a nitrogen oxide. As a catalyst for this oxidizing reaction, generally, a platinum-based catalyst is employed. The nitrogen oxide may be extracted using an extracting solvent (e.g., water), and when extracting with water, there may be used water which is separated in a lower-boiling point component separating step which will be described hereinafter. Hydroxylamine can be formed by subjecting the extracted nitrogen oxide to a hydrogenation reaction using hydrogen. Any reactor can be used for oxidizing ammonia and there is no particular retraction on the choice, but a tubular reactor is usually employed. For the extraction of the nitrogen oxide, a common apparatus may be used. As a hydrogenating reactor, an apparatus or device which is commonly employed, such as a agitation vessel-type apparatus. The reaction can be carried out in a conventional manner, such as in a continuous system, a batch system, or semi-batch system. The hydroxylamine thus obtained may be reused in the oxidizing catalyst production step or the catalyst recycling step.

(Co-oxidizing Agent)

The use of the above-described imide compound makes it possible to improve the oxidation activity without employing a co-oxidizing agent such as copper chloride, and an oxidizing reaction is catalytically facilitated even under mild conditions. Thus, a cycloalkanone can be formed through the efficient oxidation of the cycloalkane at a high selectivity. Moreover, when the cycloalkane is oxidized in the co-presence of an imide compound having a unit of the formula (I) and a co-oxidizing agent, the conversion and/or selectivity is further improved.

Examples of the co-oxidizing agent as a co-catalyst (promoter) include metal compounds, such as transition metal element-containing compounds and compounds containing a Group 13 element of the Periodic Table of Elements (e.g., boron B, Aluminum Al) typified by a boron compound. The co-oxidizing agent can be used either singly or in combination with other co-oxidizing agents.

As the transition metal element, there may be mentioned, for instance, Group 3 elements of the Periodic Table of Elements (e.g., besides scandium Sc and yttrium Y, lanthanoid elements such as lanthanum La, cerium Ce, samarium Sm; actinoid elements such as actinium Ac), Group 4 elements of the Periodic Table of Elements (e.g., titaniumTi, zirconium Zr, hafniumHf), Group 5 elements (e.g., vanadium V, niobium Nb, tantalum Ta), Group 6 elements (e.g., chromium Cr, molybdenum Mo, tungsten W), Group 7 elements (e.g., manganese Mn), Group 8 elements (e.g., iron Fe, ruthenium Ru, osmium Os), Group 9 elements (e.g., cobalt Co, rhodium Rh, iridium Ir), Group 10 elements (e.g., nickel Ni, palladium Pd, platinum Pt), and Group 11 elements (e.g., copper Cu, silver Ag, gold Au) of the Periodic Table of Elements.

Particularly, when combined with an imide compound of the formula (I), a compound containing a lanthanoid element such as Ce, a Group 4 element such as Ti, a Group 5 element such as V, a Group 6 element such as Mo and W, a group 7 element such as Mn, a Group 8 element such as Fe and Ru, a Group 9 element such as Co and Rh, a Group 10 element such as Ni, or a Group 11 element such as Cu exhibits high oxidation activity.

There is no specific restriction on the species of the co-oxidizing agent (co-catalyst or promoter) provided that it contains an element selected from the elements listed above and has the oxidizing ability. The co-oxidizing agent may be a hydroxide but is usually a metal oxide, an organic acid salt, an inorganic acid salt, a halide, a coordinated compound (complex) containing an element of those listed above, a heteropolyacid, or a salt thereof which contains an element of those listed above. Further, as the boron compound, there may be exemplified boron hydrides (e.g., borane, diborane, tetraborane, pentaborane, decaborane), boric acids (e.g., orthoboric acid, methaboric acid, tetraboric acid), borates (salts of boric acid) (e.g., nickel borate, magnesium borate, manganese borate), boron oxides such as $B_2O_3$, borazane, borazene, borazine, boron amide, boron imide, and other nitrogen-containing compounds, $BF_3$, $BCl_3$, tetrafluoroborate and other halides, and esters of boric acid (e.g., methyl borate, phenyl borate).

As the organic acid salt, there may be mentioned, for example, acetates, propionates, salts of naphthenic acid, and stearates, and examples of the inorganic acid are nitrates, sulfates, and phosphates. Moreover, as the halide, there may be exemplified chlorides and bromides.

As a ligand of the complex, there may be exemplified OH (hydroxo); alkoxy groups such as methoxy, ethoxy, propoxy and butoxy groups; acyl groups such as acetyl and propionyl groups; alkoxycarbonyl groups such as methoxycarbonyl (acetato) and ethoxycarbonyl groups; acetylacetonato, cyclopentadienyl group; halogen atoms such as chlorine and bromine; CO; CN; oxygen atom; $H_2O$ (aquo); phosphorus compounds such as phosphine (e.g., a triarylphosphine such as triphenylphosphine); and nitrogen-containing compounds such as $NH_3$ (ammine), NO, $NO_2$ (nitro), $NO_3$ (nitrato), ethylenediamine, diethylenetriamine, pyridine and phenanthroline. As to the complex or a complex salt, a single ligand or ligands of the same or different kinds may be coordinated therein.

Preferred complexes includes complexes containing a transition metal element selected from those mentioned above. The complex may be constituted of a combination of a transition metal element and a ligand that are suitably selected from teh above. For example, the preferred complex may be ceriumacetylacetonato, cobaltacetylacetonato, rutheniumacetylacetonato, or copperacetylacetonato.

A polyacid which forms the heteropolyacid contains, in many cases, at least one of the Group 5 elements or the Group 6 elements of the Periodic Table of Elements, such as V (vanadic acid), Mo (molybdic acid), and W (tungstic acid). There is no specific restriction as to the central atom. Concrete examples of the heteropolyacid are cobaltmolybdate, cobalttungstate, molybdenumtungstate, vanadiummolybdate, and vanadomolybdenumphosphate.

Incidentally, in the oxidizing catalyst, the heteropolyacid is thought to participate in a hydrogen abstraction reaction, and a cobalt-containing compound or a boron-containing compound are thought to participate in the decomposition of a peroxide.

An imide compound expressed by the formula (I) or a catalytic system comprised of the imide compound and the above-described co-oxidizing agent may be either homogeneous or heterogeneous. Further, the catalytic system may be a solid catalyst comprising a catalytic component supported on a support or carrier. The support is, in many instances, a porous support such as active carbon, zeolite, silica, silica-alumina, and bentonite. As to the amount of catalytic component supported on the support in the solid catalyst, the amount of the imide compound of the formula (1) is about 0.1 to 50 parts by weight relative to 100 parts by weight of the support. The amount of the co-oxidizing agent supported is, relative to 100 parts by weight of the support, about 0.1 to 30 parts by weight.

[Catalytic Solution-preparing Step]

In the catalytic solution preparing step, the oxidizing catalyst is mixed with other components (e.g., cycloalkane, co-oxidizing agent, solvent) in the mixing vessel 1 for adjusting the concentration of the catalyst to a predetermined value thereby to prepare the catalytic solution. The catalytic solution may be one in which all components are completely dissolved, or a dispersed system.

The ratio of the imide compound of the formula (I) to the co-oxidizing agent is, for example, imide compound/co-oxidizing agent=about 95/5 to 5/95 (molar ratio), preferably about 90/10 to 20/80 (molar ratio), and more preferably about 85/15 to 50/50 (molar ratio). Moreover, the concentration of the catalyst is adjusted to the value at an oxidizing step which will be described hereinafter, depending on the amount of the catalytic solution to be supplied.

The catalytic solution prepared in such manner is fed to an oxidizing reactor 2.

[Oxidizing Step (A)]

In the oxidizing reactor 2, a cycloalkanone is formed by reacting a cycloalkane with molecular oxygen in the presence of an oxidizing catalyst of the formula (I) (and a co-oxidizing agent).

(Cycloalkanes)

As the cycloalkane, there may be exemplified $C_{4-20}$cycloalkanes (preferably $C_{4-16}$cycloalkanes, more preferably $C_{4-10}$cycloalkanes), such as cyclobutane, cyclopentane, cyclohexanes, cycloheptane, cyclooctane, methylcyclohexanes, ethylcyclohexanes, dimethylcyclohexanes, chlorocyclohexanes, methoxycyclohexanes, cyclooctane, cyclononane, cyclododecane, cyclopentadecane, and cyclooctadecane. These cycloalkanes can be used either singly or in combination.

Included among the preferred cycloalkanes are $C_{4-10}$ocycloalkanes (preferably, $C_{5-8}$cycloalkanes), such as cyclohexane, methylcyclohexanes, and cyclooctane. Usually, cyclohexane is employed.

An oxidation method whereby a cycloalkane such as cyclohexane is converted by an oxidizing reaction at a conversion of 10% or higher has been regarded as an oxidation method of remarkable excellence. However, the use of such oxidizing catalyst makes it possible to provide cyclohexanone at a high selectivity and in a high yield (e.g., about 20 to 60%, or higher) by just stirring together with cyclohexane in an atmosphere of oxygen. Accordingly, the oxidation process described above is useful in oxidizing cycloalkanes.

(Oxygen Source)

The molecular oxygen used for the oxidation of the cycloalkane is not particularly restricted, and oxygen diluted with an inert gas such as nitrogen, helium, argon, or carbon dioxide may be employed as well as pure oxygen. From the view points of not only operability and safety but also economy, air is preferably used.

The quantity of molecular oxygen is usually, relative to 1 mol of the cycloalkane, 0.5 mol or more (e.g., 1 mol or more), preferably about 1 to 100 mol, and more preferably about 2 to 50 mol. In many instances, an excess mol of molecular oxygen is used relative to the amount of the cycloalkane.

When supplying the reactor with molecular oxygen, the reaction may be carried out in a closed system supplied with sufficient molecular oxygen in advance, or with molecular oxygen flowing continuously. In the case of continuous flow of molecular oxygen, the flow rate of oxygen is, e.g., about 0.0001 to 10 $Nm^3$/min. (e.g., 0.1 to 10 $Nm^3$/min.), and preferably about 0.01 to 5 $Nm^3$/min (e.g., 0.1 to 5 $Nm^3$/min.) per 1L unit volume.

(Reaction Solvent)

The oxidation process of the present invention can be carried out in the presence or absence of an organic solvent insusceptible to the reaction. Examples of the organic solvent are organic acids such as acetic acid and propionic acid; nitriles such as acetonitrile, propionitrile, and benzonitrile; amides such as formamide, acetamide, dimethylformamide (DMF), and dimethylacetamide; alcohols such as t-butanol and t-amyl alcohol; aromatic hydrocarbons such as benzene; halogenated hydrocarbons such as chloroform, dichloromethane, dichloroethane, carbon tetrachloride, and chlorobenzene; nitro compounds such as nitrobenzne, nitromethane, and nitroethane; esters such as ethyl acetate and butyl acetate; ethers such as dimethyl ether, diethyl ether, diisopropyl ether, dioxane, and tetrahydrofuran; and mixed solvents thereof. As the solvent, an organic acid, a nitrile, or an amide is practically employed. Incidentally, an excess of the cycloalkane can serve as the reaction solvent.

Particularly, the use of cyclohexane as the substrate and a solvent makes possible an oxidizing reaction which does not require a solvent be additionally employed and, consequently, a solvent recovering step is omitted.

The amount of the imide compound of the formula (I) can be selected from within a wide range, and may for example be about 0.001 mol (0.1 mol %) to 1 mol (100 mol %), preferably about 0.01 mol (1 mol %) to 0.5 mol (50 mol %), and more preferably about 0.05 mol to 0.30 mol relative to 1 mol of the cycloalkane, with about 0.05 to 0.25 mol of the imide compound practically employed.

The amount of the co-catalyst (co-oxidizing agent) is, e.g., about 0.001 mol (0.1 mol %) to 0.7 mol (70 mol %), preferably about 0.005 to 0.5 mol, and more preferably about 0.01 to 0.3 mol relative to 1 mol of the cycloalkane, with about 0.005 to 0.1 mol of the co-catalyst practically employed.

In the case where a heteropolyacid or a salt thereof is used as the co-oxidizing agent, the amount thereof is about 0.1 to 25 parts by weight, preferably about 0.5 to 10 parts by weight, and more preferably about 1 to 5 parts by weight relative to 100 parts by weight of the cycloalkane.

The process of the present invention is characterized in that an oxidizing reaction smoothly proceeds even under relatively mild conditions. The reaction temperature is for example 0 to 300° C., preferably about 30 to 250° C., and more preferably about 50 to 200° C. Usually, the reaction is effected at a temperature of about 70 to 180° C. Moreover, the reaction may be effected under atmospheric pressure or under applied pressure. When conducting the reaction under applied pressure, the pressure is usually about 1 to 100 atm (e.g., 1.5 to 80 atm), preferably about 2 to 70 atm, and more preferably about 5 to 50 atm. The reaction time (residence time in flow reactions) can be suitably selected from within the range of, e.g., about 30 minutes to 48 hours, preferably about 1 to 36 hours, and more preferably about 2 to 24 hours, and the choice depends on the reaction temperature and pressure.

Incidentally, it is possible to raise the rate of oxidation reaction by effecting the reaction at a higher reaction temperature and/or under higher reaction pressure, but a carboxylic acid or a peroxide may sometimes be by-produced.

In the presence of or in a stream of molecular oxygen, the oxidizing reaction can be carried out in a conventional manner, such as in a batch system, a semi-batch system, or a continuous system. The reaction may be carried out by reactive distillation accompanied by removal of water, or by a reactive distillation involving employing a water-separating apparatus, such as a decanter 5a used in a lower-boiling point component separating step which will be described later, in combination with the reactor for removing water. As the apparatus, use can be made of a conventional one. When employing a continuous system reactor or semi-batch system reactor, either one of the cycloalkane or molecular oxygen (or a gas containing molecular oxygen), or both components may be supplied from one or a plurality of supply ports. Further, the port(s) from which the reaction components are supplied may be made in the form of a nozzle for raising the mixing efficiency. The order of addition of the components is not particularly restricted and these can be added in any order. The reactor may be constituted of a single or more than two vessels connected serially.

[Catalyst Separating-step (B1)]

Using one or a plurality of filters 3, after the reaction mixture in the oxidizing reaction 2 is cooled if necessary, the precipitated catalyst (e.g., N-hydroxyphthalimide) is filtered out. The cooling or filtering temperature is about 0 to 100° C., preferably about 5 to 70° C., and more preferably about 10 to 50° C. The treatment procedure in this step can be performed continuously, batchwise, or semi-batchwise. As the filter, conventional ones such as centrifugal filters and filter presses are available.

Moreover, the separated catalyst (containing the co-oxidizing agent) may be recycled to the reaction system, or may be reused after the co-oxidizing agent (e.g., a transition metal such as cobalt) has been recovered therefrom by subjecting the catalyst to incineration. In this embodiment, the reaction mixture from which the catalytic component has been separated by the filter 3 is subjected to a separating step of the acid component (B2) and then to a separating step of the lower-boiling point component (C1).

Incidentally, in the catalyst separating step, the catalyst is separable by a conventional means (e.g., filtration, distillation, crystallization).

[Acid Component Separating Step (B2)]

The reaction mixture sometimes contains a by-produced higher-boiling point acid component or a derivative thereof (e.g., esters). Therefore, the reaction mixture is usually subjected to a separating step of the lower-boiling point component after the higher-boiling point acid component has been removed by extraction or distillation in an extraction column 4. When employing water as an extracting solvent, the extracted component constituted of the higher-boiling point acid and water may be reused in an impurities-removing step by hydrolysis or the like which will be described later.

Furthermore, the extraction may be conducted by distillation (extraction distillation). As the extractor, use distilling column 6 is recycled to the mixing vessel 1 or oxidizing reactor 2. The water separated in the decanter 5a may be drained, but it may be used as extracting water for recovering the nitrogen oxide in the production step of the raw material (hydroxylamine) of the catalyst.

The number of plates of the distilling column (recovering column) may for example be about 5 to 80, preferably about 20 to 60. The distilling operation may be conducted at an overhead temperature of about 5 to 180° C. (preferably, about 40 to 120° C.), a bottom temperature of about 50 to 250° C. (preferably, about 70 to 150° C.) and at a pressure of 1 mmHg to 20 atm (preferably, about 100 mmHg to 5 atm), depending on the species of the cycloalkane. The distilling operation is conducted in a conventional manner, e.g., by refluxing the distillate at a suitable reflux ratio (e.g., about 0.1 to 50, preferably about 1 to 20).

For the separation of the lower-boiling point component, a conventional separation means may be employed, such as condensation, distillation, evaporation, and extraction, or a combination thereof. When separating the lower-boiling point component, the lower-boiling point component may be separated from the reaction mixture by azeotropy. Moreover, though the lower-boiling point component can be separated from the reaction mixture merely by distilling the reaction mixture and the separation may be carried out in a single separation step, a multiple separating step is advantageous for separating the cycloalkane. If needed, water and the cycloalkane cut may be can be made of an apparatus which is commonly employed, and such apparatus may be employed singly or in combination with other ones.

[Lower-boiling Point Component Separating Step (C1)]

The reaction mixture in the oxidizing reactor 2 contains the lower-boiling point component (comprised of, e.g., the cycloalkane left unreacted, water, solvent, lower-boiling point impurities) and the higher-boiling point component (comprised of, e.g., cycloalkanone, cycloalkanol, higher-boiling point impurities). In FIG. 1, separation of the lower-boiling point component (containing lower-boiling point impurities) from the reaction mixture from which the acid component has been eliminated is effected using one or a plurality of distilling columns (distilling columns 5 and 6). Through this distilling operation, a component containing the cycloalkanone and cycloalkanol (higher-boiling point component) and a distillate containing the lower-boiling point component constituted of the cycloalkane, water, and the like are distilled off from the bottom and the overhead of the first distilling column 5, respectively. In the second distilling column 6, a distillate from the overhead of the first distilling column 5 is separated into the cycloalkane which is distilled from the bottom and the lower-boiling point impurities which is distilled from the overhead. The distillate from the overhead of the first distilling column 5 is fed to the distilling column 6 via the decanter 5a for separation of water.

Furthermore, the cycloalkane separated in the second separated from each other by cooling the cut (lower-boiling point component) distilled in the distilling column 5 and then liquid-separating the water contained in the cut (using a decanter or the like). Although the cycloalkane cut is reusable as a raw material for the oxidizing reaction system even without purification, the cycloalkane cut, which is made much purer by removing impurities therefrom, is also reusable as a raw material for the reaction.

[Impurities Separating Step (a step for Separating a Derivative of the Acid Component) (B3)]

The mixture from which the lower-boiling point component has been separated by the first distilling column 5 sometimes contains a derivative (e.g., esters) of the higher-boiling point acid component (e.g., carboxylic acids) by-produced in the oxidizing reaction, and the like. For separating such impurities, it is preferred that the reaction mixture from which the lower-boiling point component has been separated is subjected to an impurities separating step. A cycloalkane and cycloalkanol of higher purity are yielded through such operation.

In FIG. 1, the reaction mixture from which the lower-boiling point component has been separated is fed to a hydrolyzing column 7 for hydrolyzing treatment. With water contained in the mixture being refluxed, the treated solution is neutralized and/or saponified using an alkali or a salt thereof in a neutralizing and/or saponifying column 8. Since the aqueous phase in the hydrolyzing column 7 sometimes contains higher-boiling point impurities (e.g., catalystic component(s)), the aqueous phase is fed to a catalyst-recovering unit 11, and the organic phase (the reaction mixture from which impurities have been removed) in the neutralizing and/or saponifying column 8 is subjected to a higher-boiling point component separating step after moisture has been separated from the phase by a liquid-separator (decanter 8a)

The elimination of impurities resulted from the hydrolysis, or the neutralization and/or saponification may be effected by distillation or reactive distillation. Moreover, it is also possible to eliminate the impurities by evaporation, extraction, extractive distillation, neutralization, or saponification, using water, an alkali, or a salt thereof. A combination of these operations is advantageous for eliminating the impurities more efficiently. The neutralization or saponification may be carried out, using water or an alkali or a salt thereof, in a continuous system, a batch-system, or a semi-batch system.

At this step, the temperature for saponification is about 50 to 200° C., preferably about 80 to 150° C. The pressure is about 0.001 to 20 atm, preferably about 0.1 to 15 atm.

There is no particular restriction on the choice of the species of the alkali or a salt thereof, and examples of which are hydroxides or salts of alkaline metals (e.g., lithium, sodium, potassium) or alkaline earth metals (magnesium, calcium), such as alkaline metal hydroxides (e.g., lithium hydroxide, sodium hydroxide, potassium hydroxide), alkaline metal hydrogencarbonates (e.g., lithium hydrogencarbonate, sodium hydrogencarbonate, potassium hydrogencarbonate), alkaline metal carbonates (e.g., lithium carbonate, sodium carbonate, potassium carbonate), alkaline earth metal hydroxides (e.g., magnesiumhydroxide, calciumhydroxide), and alkaline earth metal carbonates (e.g., magensium carbonate, calcium carbonate). If necessary, ammonia or an organic base (e.g., amines) may be used. Preferred alkalis are alkaline metal hydroxides (e.g., lithium hydroxide, sodium hydroxide, potassium hydroxide).

As an aqueous solution (or slurry) of the alkali, usually, use can be made of an aqueous solution having a pH of about 7 or higher (preferably about 7 to 10).

Though the concentration of the alkaline solution (or slurry) can be selected from within a wide range, it is usually selected from within the range in which handling easiness is kept good. The concentration is, e.g., about 1 to 90% by weight, preferably about 5 to 60% by weight, and more preferably about 10 to 30% by weight.

[Higher-boiling Point Component Separating Step (Separating Step of Cycloalkanone (C2)]

The reaction mixture from which the lower-boiling point component and impurities have been removed contains the cycloalkanone and the cycloalkanol, and impurities having higher-boiling points, such as the by-product(s) and the catalyst (including the co-catalyst), may sometimes be left. Therefore, the reaction mixture is subjected to a higher-boiling point component separating step (separating step using distilling columns 9 and 10) to separate the reaction mixture into the cycloalkanone, cycloalkanol, and the higher-boiling point impurities (e.g., by-product, oxidizing catalyst, co-oxidizing agent).

That is, in FIG. 1, the higher-boiling point components are separated by supplying the distillate from the bottom of the first distilling column 9 to the second distilling column 10 and distilling off the cycloalkanone and the higher-boiling point impurities from the overhead and the bottom, respectively. Moreover, in the distilling column 10, the cycloalkanol is separated by side-cut (e.g., from a plate positioning at a height of 10 to 80% of the number of plates from the bottom). In this embodiment, the cycloalkanol separated by the distilling column 10 is recycled to the reaction system in the reactor 2 to be converted into a cycloalkanone there. Accordingly, it is possible to form cycloalkanones efficiently without a dehydrogenating step. Incidentally, lower-boiling point impurities contained in the organic phase in the saponifying step are distilled from the overhead of the first distilling column 9.

As was described above, in the case where a product resulted from the treatment by means of extraction, hydrolysis, saponification, or neutralization in the impurities-removing step (moderate-boiling point impurities) is left in the reaction mixture, through a distilling operation utilizing the first distilling column 9, the moderate-boiling point impurities are removable in advance of the separation of the cycloalkanone and cycloalkanol.

The number of plates of the distilling column (recovering column) may be about 5 to 80, preferably about 20 to 60. The distilling operation can be conducted at an overhead temperature of about 5 to 200° C. (preferably, 40 to 120° C.), a bottom temperature of about 50 to 250° C. (preferably, about 70 to 150° C.) and a pressure of about 1 mmHg to 20 atm (preferably, 100 mmHg to 5 atm), and the choice depends on the species of the cycloalkanone. The distillation may be performed in a conventional manner, for example, by refluxing the distillate at a suitable reflux ratio (e.g., about 0.1 to 50, preferably about 1 to 20).

It matters nothing if the higher-boiling point impurities separated from the bottom of the distilling column 10 is incinerated for disposal. However, in the case where the higher-boiling point impurities contain a co-oxidizing agent (e.g., transition metals such as cobalt), the co-oxidizing agent contained therein can be made reusable by supplying the higher-boiling point impurities to a catalyst-recovering unit 11 for separation.

Incidentally, a means whereby the higher-boiling point component is separated is not limited to the above-mentioned distilling means, and a conventional separation means such as condensation, distillation, evaporation, and extraction, or a combination of thereof may be employed. Preferred separation means include at least distillation means. Moreover, the moderate-boiling point impurities and the cycloalkanol can be distilled from the overhead and the bottom of the distilling column 9, respectively, and the cycloalkanone can be separated by side-cut.

Furthermore, the higher-boiling point component may be separated in a single or a multiple distilling or separating step. For providing a cycloalkane and cycloalkanol of higher purity, it is advantageous to effect the separation of the higher-boiling point impurities in combination with that of the moderate-boiling point impurities.

[Catalyst-regenerating Step]

The catalytic component in the reaction mixture is separated at the catalyst-separating step (B1), the impurities-separating steps (B1 and B2), and the higher-boiling point component separating step (C2). The separated oxidizing catalyst is supplied to a catalyst-recycling unit 13 to be regenerated there. The oxidizing catalyst denatured or deteriorated in activation by the reaction can be regenerated by treating or reacting the catalyst with hydroxylamine or an acid, because the denatured oxidizing catalyst is mainly constituted of a polycarboxylic acid corresponding to the imide compound, or an acid anhydride thereof (e.g., phthalic acid imide, phthalic anhydride). As hydroxylamine, the hydroxylamine prepared in the hydroxylamine-producing step may be used. Moreover, free hydroxylamine or a salt of hydroxylamine (e.g., sulfates) may be used. The regenerating reaction may be effected by reactively distilling the reaction mixture while removing ammonium resulting from the reaction. Examples of the acid are hydrogen halides typified by hydrogen chloride and hydrogen bromide; inorganic acids typified by hydrofluoric acid, hydrochloric acid, hydrobromic acid, sulfuric acid, nitric acid, and phosphoric acid; and sulfonic acids typified by benzenesulfonic acid and p-toluenesulfonic acid. It is preferred that the acid is anhydrous.

The reaction, as in the oxidizing catalyst-producing step, can be effected in a conventional manner, such as in a batch-system, semi-batch system, or a continuous system. As the reactor, a reactor which is similar to the one used above can be employed, and the reactor can be used either singly or in combination with other reactors. Furthermore, any conventional apparatus can serve as the reactor, and the reactor used in the catalyst-producing step may be utilized as it is.

It is possible to use the obtained oxidizing catalyst (N-hydroxyphthalimide), as it is, as a catalyst of the catalytic solution-preparation step.

Recovery of the metal component from the co-oxidizing agent mentioned above allows the co-oxidizing agent to serve as the catalyst of the catalytic solution-producing step.

Figure 2:
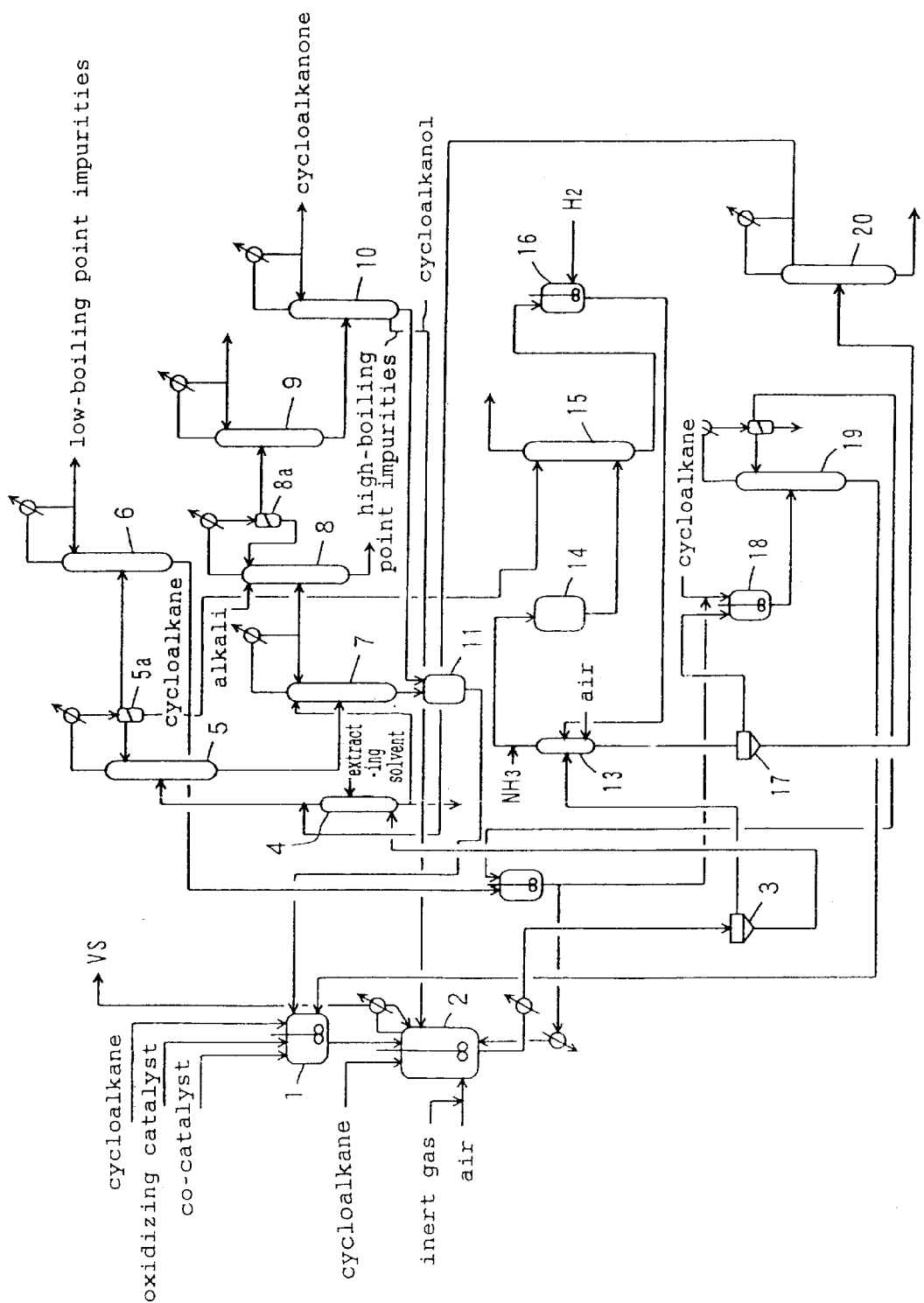
FIG. 2 is a flow-chart for explaining another process of the present invention.

FIG. 2 is a flow chart showing another embodiment of the present invention. Except for the catalyst-regenerating process for regenerating the catalyst denatured or deteriorated in activity by the reaction, the process of this embodiment is basically common to the process shown in FIG. 1. That is, the catalytic component separated from the reaction mixture by means of the catalyst-separation unit 3 such as filter is fed to the catalyst-regenerating unit 13. In the catalyst-regenerating unit 13, the catalytic component [e.g., a polycarboxylic acid corresponding to the imide compound, or an acid anhydride thereof (phthalic imide, phthalic anhydride, or the like] denatured or deteriorated in activity is recycled by treating or reacting with hydroxylamine. The recycling reaction is carried out while supplying oxygen or air and removing ammonia which is produced in the reaction.

The hydroxylamine can be obtained in the following manner. That is to say, in an ammonia oxidizing unit 14, ammonia (this may be ammonia which is produced in the catalyst-regenerating unit 13) is oxidized with molecular oxygen to form a nitrogen oxide NOx. As a catalyst for this oxidizing reaction, a platinum-based catalyst is generally employed. The nitrogen oxide NOx is recovered in a recovering column 15. The NOx can be recovered through an extracting operation using an extracting solvent (e.g., water), a crystallizing operation, or a distilling operation. Hydroxylamine is produced by hydrogenating the recovered nitrogen oxide NOx in a reactor 16. The hydroxylamine thus obtained is fed to the catalyst-regenerating unit 13.

The catalyst (imide compound) recycled in the catalyst-recycling unit 13 is separated by a separation unit 17 such as a filter, mixed with a cycloalkane if needed, and then reserved in a tank 18. When using the catalyst in the tank 18, it is supplied to a dehydrating tower 19, dehydrated, and fed to the mixing vessel 1 for the preparation of the catalyst. On the other hand, a non-catalytic component separated by the separation unit 17 is supplied to a distilling column 20, and the distillate (lower-boiling point component) from the overhead can be subjected to the separating step of the lower-boiling point component.

[Solvent-removing or Recovering Step]

When employing a solvent in the oxidizing reaction of the present invention, according to the boiling point of the solvent, the solvent may be separated and recovered in a suitable step (e.g., the lower-boiling point- or higher-boiling point component separating step), or it may be separated and recovered by additionally employing a solvent-recovering unit. The separated solvent may be recycled to the reaction system, or may be used for preparation of the above-mentioned catalytic solution.

Figure 3:
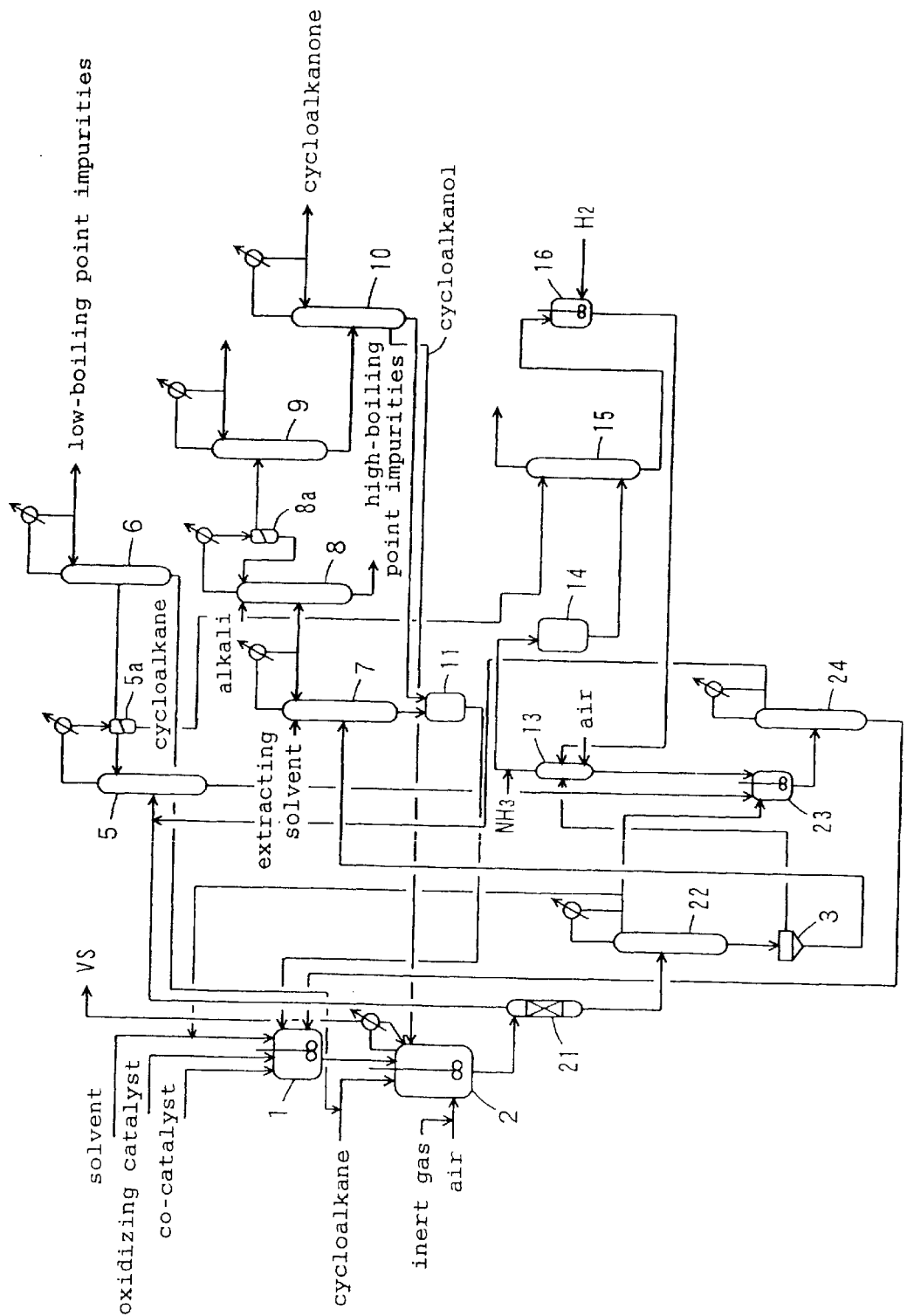
FIG. 3 is a flow-chart for explaining still another process of the present invention.

FIG. 3 is a flow chart showing still another embodiment of the present invention. In this embodiment, there is shown a process for separating and recovering a solvent for the case where a solvent having a boiling point higher than that of a lower-boiling point distillate (e.g., acetic acid) such as a cycloalkane is used.

That is to say, the reaction mixture from the reaction unit 2 is supplied to an evaporator 21, and a lower-boiling point distillate from the overhead of the evaporator 21 is subjected to the same lower-boiling point component separating step as described above. On the other hand, a distillate from the bottom of the evaporator 21 (e.g., catalytic component, higher-boiling point component, solvent) is fed to a desolventing column 22, and a distillate from the bottom of the desolventing column 22 is supplied to the catalyst-separation unit 3. The catalytic component separated in the separation unit 3 is fed to a catalyst-regenerating unit 13 similar to the one described above. Without being subjected to the above-described acid component separating step, the higher-boiling point component from which the catalytic component has been removed by the catalyst-separating unit 3 is subjected to, via the hydrolyzing column 7 and the saponifying column 8, a higher-boiling point component separating step similar to the one described above.

On the other hand, part of a distillate from the overhead of the desolventing column 22 is recycled to the reaction system for use as a solvent and, in a mixing tank 23, the rest of the distillate is mixed with the catalyst regenerated in the catalyst-regenerating unit 13 and the distillate from the bottom of the first distilling column 5 of the lower-boiling point component-separating step. Thereafter, the resultant mixture in the mixing tank 23 is fed to a distilling column 24 for recovering and dehydrating the catalytic component. A distillate from the overhead of the distilling column 24 is subjected to the above-described lower-boiling point component separating step, and a distillate from the bottom of the distilling column 24 is fed to the above-described mixing vessel for the preparation the catalytic solution.

When a solvent having a boiling point equal to or lower than the boiling point of a lower-boiling point component such as the cycloalkane is employed, it is possible to recover the solvent in the lower-boiling point component separating step (e.g., by the first distilling column) and reuse as the reaction solvent. Moreover, when a solvent having a boiling point higher than the boiling points of the cycloalkanone and the cycloalkanol is employed, a component containing the solvent may be subjected to the oxidation step or catalytic solution preparing step after the cycloalkanone and cycloalkanol have been separated.

In the present invention, the reaction mixture of the oxidizing reactor 2 may be separated into the lower-boiling point component containing the cycloalkane and the higher-boiling point component containing the cycloalkanone and cycloalkanol without being subjected to the catalyst-separating step.

Figure 4:
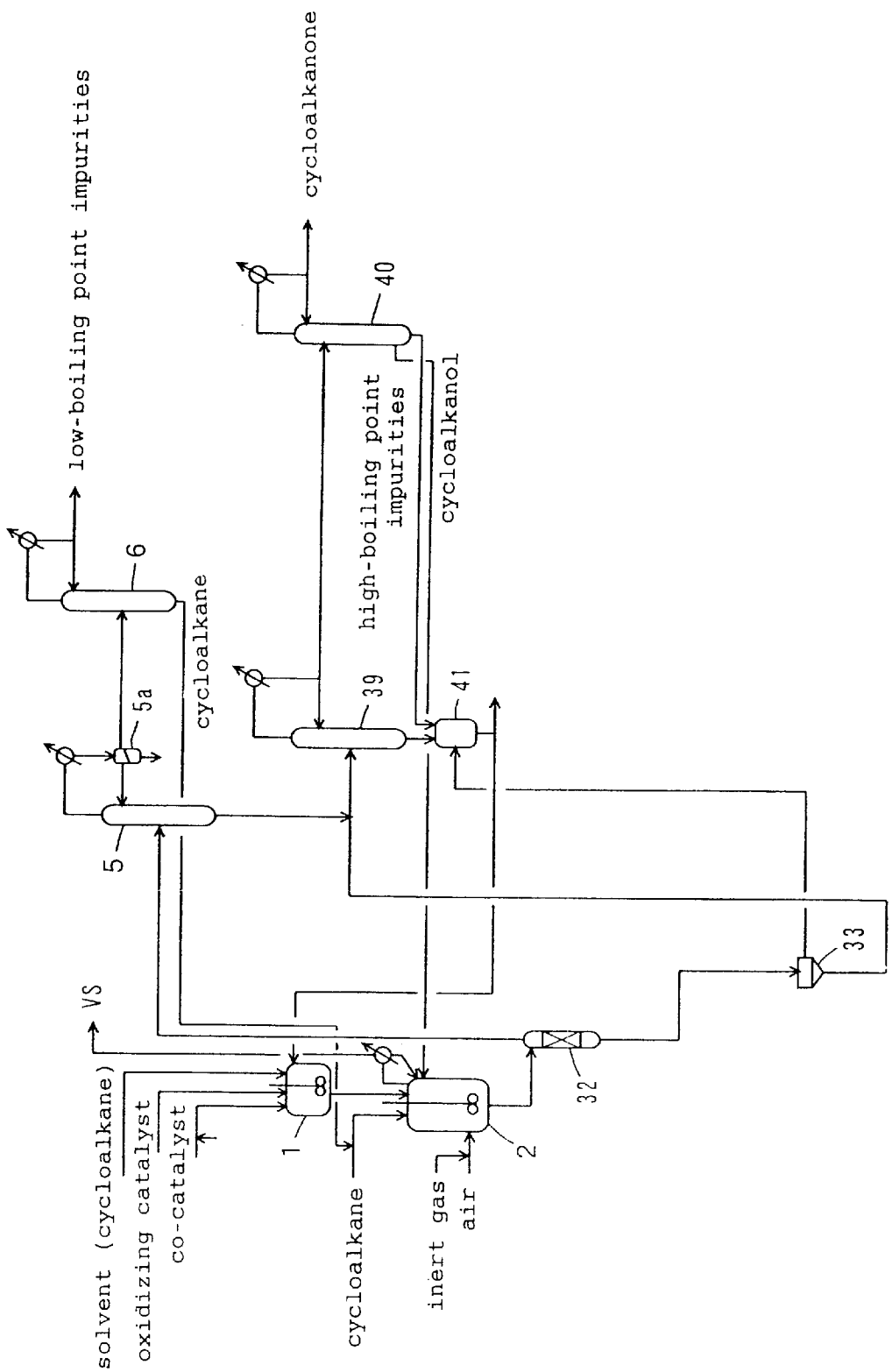
FIG. 4 is a flow-chart for explaining another process of the present invention.

FIG. 4 is a flow chart illustrating another embodiment of the present invention. In this embodiment, the reaction mixture in the oxidizing reactor 2 is supplied to a distilling column 32 for separating the mixture into the lower-boiling component and the higher-boiling component. Similar to the above, a lower-boiling point cut from the overhead of the distilling column 32 is fed to the first distilling column 5 and the second distilling column 6 for separating the cycloalkane and the lower-boiling point impurities from each other, and subjected to the lower-boiling point component-separating step (C1).

On the other hand, a higher-boiling point distillate from the bottom of the distilling column 32 (catalytic component, higher-boiling point component) is, if needed, cooled and filtrated by a single or a plurality of filters 33 thereby to filter off the precipitated catalyst. The resultant reaction mixture from which the catalytic component has been removed is fed to the distilling column 39 for separating the higher-boiling point component and the higher-boiling point impurities from each other. Similar to the above, a distillate from the overhead of the distilling column 39 is supplied to a distilling column 40 and subjected to the higher-boiling point component separating step (C2) for separating the cycloalkanone and cycloalkanol from each other. The separated cycloalkanol is recycled to the reactor 2. Moreover, higher-boiling point impurities from the bottom of a distilling column 39 contains the catalyst, a higher-boiling point acid component or a derivative thereof. Therefore, in this embodiment, the cut having a higher-boiling point distilled from the bottom of the distilling column 39 is supplied to a catalyst recovering unit 41. Similar to the above, the higher-boiling point impurities may be subjected to the separation steps for separation into the catalyst and acid component or a derivative thereof.

Incidentally, in the present invention, the hydroxylamine-producing step, oxidizing catalyst-producing step, catalytic solution-preparing step, lower-boiling point component separating step, catalyst-regenerating step, and the solvent-removing or recovering step is not necessarily required, but a combination of the steps (A)(B)(C) with the lower-boiling point component separating step is advantageous f or providing cycloalkanones with high efficiency and the catalytic solution-preparing step makes it possible to provide cycloalkanones steadily.

The order of the steps is not particularly restricted and the order may be different from the process described above. For example, after the lower-boiling point component is separated from the reaction mixture, from the resultant mixture may be separated the catalyst, the acid component or a derivative thereof, and the higher-boiling point component, followed by the separation of the cycloalkane from the higher-boiling poing component. There is also proposed another option of separating the catalyst and the acid component or a derivative thereof from the reaction mixture and then separating the lower-boiling point component and the higher-boiling point component from the reaction mixture from which the impurities have been removed. It is not necessary to separate the catalyst and by-produced acid component or a derivative thereof individually, and may be removed in one step. Moreover, in the present invention, the cycloalkane, the cycloalkanol, and the catalyst are not necessarily recycled.

In the oxidizing reaction or hydrolyzing or saponifying step, as the reaction apparatuses, conventional ones are available, and the shape of the apparatus may be spherical or columnar. The reaction apparatus does not require a particular mechanism inside. However, the apparatus may be equipped with a unit for control of mixing, such as a draft, or members such as perforated plates with which the inside of the apparatus is separated into a plurality of chambers. Moreover, for raising the stirring efficiency, the apparatus may be equipped with a mechanical stirrer such as stirring blades. Further, a single or a plurality of reaction vessels may be used for the reaction. Furthermore, as the distilling columns and extraction-distilling column, there may be used a plate column, a perforated-plate column, a packed tower (regular packed tower, irregular packed tower), a bubble tower, or a valve tower. As the extractor, there may be exemplified conventional ones, such as mixer-settlers, perforated-plate columns, spray towers, packed towers, ring & plate towers, rotary-disc extraction column, and curl columns. As the evaporator, conventional ones such as natural circulation type-evaporators, horizontal-tube evaporators, natural circulation-type short-tube vertical evaporators, horizontal-tube descending film-type evaporators, long-tube vertical descending film-type evaporators, forced circulation horizontal tube-type evaporators, forced circulation vertical tube-type evaporators, and agitated film evaporators. A single or a plurality of apparatuses may be used, and these may be used either singly or as a combination of two or more kinds of apparatuses.

INDUSTRIAL APPLILICABILITY

According to the present invention, since a specific oxidizing catalyst is used for the oxidation of a cycloalkane, it is possible to efficiently produce a cycloalkanone using a set of production equipment without involving a dehydrogenating step. Moreover, the present invention makes it possible to produce cycloalkanones at a high conversions and high selectivities even under mild conditions, and to effectively utilize a catalyst without deteriorating the activity of the catalyst. Furthermore, exhaust gas treatment is unnecessary, the present invention can provide cycloalkanones with economical advantages.

EXAMPLES

Hereinafter, the present invention will be described in further detail and should by no means be construed as defining the scope of the invention.

Example 1

(1) Catalytic Solution-preparing Step

A catalytic solution was prepared in proportions of cyclohexane 10,000 g/H, N-hydroxyphthalimide 10 g/H, and cotaltacetonato 64 g/H.

(2) Oxidation Step

The catalytic solution prepared in the above proportion, cyclohexane, and air were fed to a reactor 2 at rates of supply of 840 g/H and 1.3 $Nm^3/H$, respectively, and the mixture was reacted at 160° C. and 40 atm for a residence time of two hours. At a conversion of 11%, the cyclohexane was converted into a cyclohexanone and a cyclohexanol at selectivities of 40% and 49%, respectively.

(3) Catalyst-separating Step

The crude reaction mixture was cooled to 20° C., and the catalyst was separated by filtration at a rate of 9.8 g/H. The separated catalyst was treated by incineration to recover the cobalt contained therein and then recycled to the reaction system for reuse. In an extraction column 4 equipped with rings and plates, the filtrate was subjected to an extraction step with water at 20° C. to extract an acid having a higher-boiling point and the like.

(4) Lower-boiling Point Component Separating Step

In a perforated-plate column 5 with 30 column plates, the organic phase was separated into cyclohexane/cyclohexanol (KA oil) and the higher-boiling point component by means of azeotropy of water and cyclohexane. The distillate was separated into the aqueous phase and the cyclohexane phase by a decanter, and then water was removed. In a perforated-plate column 6 with 30 column plates, the lower-boiling point component was separated from the cyclohexane phase. The cyclohexane from the bottom was recycled to the reaction system.

(5) Impurities-separating Step

As to the solution of the KA oil and the higher-boiling point component, an ester having a higher-boiling point was hydrolyzed, using an acidic aqueous solution of the acid having a higher-boiling point obtained above and a perforated-plate column 7 with 30 column plates, to separate part of the higher-boiling point acid. The separated acid was then incinerated. As to the distillate, using a perforated-plate column 8 with 40 column plates and a solution comprised of 5% by weight of a sodium hydroxide aqueous solution and 5% by weight of sodium carbonate aqueous solution mixed in a ratio of 1 to 1, the acid and ester having higher-boiling points were then saponified or neutralized and removed. The distillate was separated into the aqueous phase and the KA oil phase by using a decanter, and the water separated was refluxed.

(6) Higher-boiling Point Component Separating Step

As to the KA oil phase, the moderate-boiling point component was separated using a bubble tower 9 with 20 column plates. Using a perforated-plate column 10 with 60 column plates, the product cyclohexanone was collected from the reaction mixture comprised of the KA oil and the higher-boiling point component. According to this process, the purification efficiency was 90%, and the purity of the product was 99%.

Further, cyclohexanol collected from the 50th column plate from the top and recycled to the reaction system was capable of easily converting cyclohexanone in a 98% yield. Without using a dehydrogenator, the higher-boiling point component from the bottom of a perforated-plate column 10 was incinerated for disposal.

Example 2

(1) Catalysti Solution-preparing Step

A catalytic solution was prepared in proportions of cyclohexanone 1,000 g/H, N-hydroxyphthalimide 160 g/H, and cobalt acetonato 64 g/H.

(2) Oxidation Step

The catalytic solution prepared in the above proportion, cyclohexane, and air were fed to a reactor 22 at rates of supply of 840 g/H and 1.3 Nm$^3$/H, respectively, and the mixture was reacted at 160° C. and 40 atm for a residence time of four hours. At a conversion of 32%, cyclohexane was converted into a cyclohexanone and a cyclohexanol at selectivities of 89% and 5%, respectively.

(3) Catalyst-separating Step

The crude reaction mixture was cooled to 20° C., and the catalyst was separated by filtration at a rate of 158 g/H. In an extraction column 24 equipped with rings & plates, the filtrate was subjected to an extraction step with water at 20° C. to extract an acid having a higher-boiling point and the like.

(4) Lower-boiling Point Component-separating Step

In a perforated-plate column 25 with 30 column plates, the organic phase was separated into KA oil and the higher-boiling point component by means of azeotropy of water and cyclohexane. The distillate was separated into the aqueous phase and the cyclohexane phase by a decanter. In a perforated-plate column 26 with 30 column plates, the lower-boiling point component was separated from the cyclohexane phase. The cyclohexane from the bottom was recycled to the reaction system for reuse.

(5) Impurities-separating Step

As to the solution of the KA oil and the higher-boiling point component, an ester having a higher-boiling point was hydrolyzed, using an acidic aqueous solution of the acid having a higher-boiling point obtained above and a perforated-plate column with 30 column plates, to separate part of the higher-boiling point acid. The separated acid was then incinerated. As to the distillate, using a perforated-plate column with 40 column plates and a solution comprised of 5% by weight of a sodium hydroxide aqueous solution and 5% by weight of sodium carbonate aqueous solution mixed in a ratio of 1 to 1, the acid and ester having higher-boiling points were then saponified or neutralized and then removed. The distillate was separated into the aqueous phase and the KA oil phase by using a decanter, and the water separated was refluxed.

(6) Higher-boiling Point Component Separating Step

As to the KA oil phase, the moderate-boiling point component was separated using a bubble tower 29 with 20 column plates. Using a perforated-plate column 210 with 60 column plates, the product cyclohexanone was collected from the reaction mixture comprised of the KA oil and the higher-boiling point component. The purification yield of was 91% and the purity of the product was 99%.

Cyclohexanol, collected from the 50th column plate from the top and then recycled to the reaction system, was capable of easily converting cyclohexanone in a 97% yield. A dehydrogenator, which is conventionally required, was no longer necessary. The higher-boiling point component was incinerated to recover the cobalt contained therein and then recycled to the reaction system for reuse.

(7) Catalyst-regenerating Step and Catalyst Material-producing Step

As to the catalyst, the catalyst was regenerated using hydroxylamine and a perforated-plate column with 30 column plates (regeneration rate: 95%). The regenerated catalyst was recycled to the reaction system after moisture has been eliminated therefrom by a perforated-plate column with 30 column plates, and then reused. Moreover, the cyclohexane in the catalyst was also recycled to the reaction system for reuse. As to the hydroxylamine which is used when regenerating the catalyst and producing the catalyst, it was produced by effecting an oxidizing reaction in which, using a platinum-based catalyst, ammonia by-produced upon the regeneration of the catalyst is oxidized in a tube reactor to form an $NO_x$ (e.g., $NO_2$, $N_2O_3$, $N_2O_5$), absorbing the $NO_x$ with rings & plates using the water separated in the lower-boiling point component separating step, and then carrying out a hydrogenating reaction.

Example 3

(1) Catalytic Solution-preparing Step

A catalytic solution was prepared in proportions of acetic acid 1,000 g/H. N-hydroxyphthalimide 160 g/H, and cotalt acetonato 64 g/H.

(2) Oxidation Step

The catalytic solution prepared in the above proportion, cyclohexane, and air were fed to a reactor 32 at rates of supply of 840 g/H and 1.3 Nm$^3$/H, respectively, and the mixture was reacted at 75° C. and 40 atm for a residence time of 4 hours. At a conversion of 31%, the cyclohexane was converted into a cyclohexanone and a cyclohexanol at selectivities of 90% and 5%, respectively.

(3) Lower-boiling Point Component Separating Step

In a forced circulation-type evaporator, the crude reaction mixture was separated into the lower-boiling point component comprised of cyclohexane, water and others, and the higher-boiling point component comprised of acetic acid, the KA oil, the catalyst and others. Using a perforated-plate column with 30 plates, water and the cyclohexane were separated from the lower-boiling point component by azeotropy, and the resultant mixture was separated into the aqueous phase and the cyclohexane phase by using a decanter. A lower-boiling point component was separated from the cyclohexane phase in a perforated-plate column with 30 plates and the cyclohexane from the bottom was recycled to the reaction system for reuse.

(4) Solvent-separating Step

Acetic acid was separated from the higher-boiling component comprised of acetic acid, the KA oil, the catalyst and others using a perforated-plate column with 30 column plates, and recycled to the reaction system for reuse.

(5) Impurities-separating Step

The higher-boiling point component comprised of the KA oil, catalyst and others was cooled to 20° C., and then the catalyst was separated by filtration at a rate of 158 g/H. Using a perforated-plate column with 30 column plates, the ester with a higher-boiling point contained in the filtrate was hydrolyzed with water to separate part of the higher-boiling point acid, and the separated acid was subjected to incineration treatment. As to the distillate, using a perforated-plate column with 40 column plates and a solution comprised of 5% by weight of a sodium hydroxide aqueous solution and 5% by weight of sodium carbonate aqueous solution mixed in a ratio of 1 to 1, the acid and the ester each having a higher-boiling point were saponified or neutralized, and then removed.

(6) Higher-boiling Point Component Separating Step

The distillate was separated into the aqueous phase and the KA oil phase in a decanter, and the water separated was refluxed. The moderate-boiling point component was separated from the KA oil phase using a bubble tower with 20 column plates. From the KA oil and the higher-boiling point component, the product cyclohexanone was collected using a perforated-plate column with 60 column plates. In the production process, the purification yield was 91% and the purity of the product was 99%.

Cyclohexanol, collected from the 50th plate from the top and recycled to the reaction system, was capable of easily converting a cyclohexanone in a 97% yield, with consequent omission of a dehydrogenator. The higher-boiling point component was incinerated to recover the cobalt therefrom, and the recovered cobalt was recycled to the reaction system for reuse.

(7) Catalyst-regenerating Step

As to the catalyst, the catalyst was regenerated using hydroxylamine and a perforated-plate column with 30 column plates. After moisture has been removed, the regenerated catalyst was recycled to the reaction system for reuse. Among the catalysts subjected to the reaction, although the amount of a catalyst denatured or deteriorated in activity was small, it was treated for regeneration, and the denatured or deactivated catalyst was ascertained to give no influence on the reaction. Moreover, the cyclohexane in the catalyst was also recycled to the reaction system and reused. As to the hycroxylamine for use in regenerating and producing the catalyst, the hydroxylamine was produced by oxidizing, in a tube reactor, ammonia by-produced upon the regeneration of the catalyst with a platinum-based catalyst to give an $NO_x$ (e.g., $NO_2$, $N_2O_3$, $N_2O_5$); absorbing the NOx using rings & plates and water; and carrying out a dehydrogenation reaction.

What is claimed is:

1. A process for producing a cycloalkanone from a cycloalkane in an oxidizing reaction system using an oxidizing catalyst having an imide unit represented by the following formula (I):

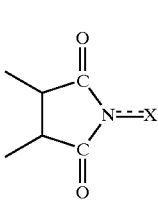

wherein X represents oxygen atom or hydroxyl group, which comprises
(A) a step for bringing the cycloalkane into contact with molecular oxygen in the presence of the oxidizing catalyst,
(B) a step for separating the catalyst, and a by-produced acid component or a derivative thereof from the reaction mixture,
(C) a step for separating a first component containing the cycloalkane and a second component which has a boiling point higher than that of the first component and contains the cycloalkanone and the cycloalkanol from the reaction mixture, and
(D) a step for separating the cycloalkanone and the cycloalkanol from the second component and then recycling the separated cycloalkanol to the oxidizing reaction system.

2. A process according to claim 1, wherein the cycloalkane and impurities are separated from the first component; and the cycloalkanone, the cycloalkanol, and impurities are separated from the second component.

3. A process according to claim 1, wherein an acid component or a derivative thereof is separated by at least one means selected from the group consisting of extraction, hydrolysis, saponification, and neutralization.

4. A process according to claim 1, wherein the cycloalkanone and the cycloalkanol are separated from a component containing a product resulted from the extraction, hydrolysis, saponification, or netralization.

5. A process according to claim 1, which comprises at least one step selected from the group consisting of:
a step for producing hydroxylamine;
a step for producing an oxidizing catalyst recited in claim 1;
a step for preparing a catalytic solution containing an oxidizing catalyst recited in claim 1; and
a step for regenerating the catalyst subjected to the reaction.

6. A process according to claim 1, wherein the cycloalkane is a $C_{4-10}$cycloalkane.

7. A process according to claim 1, wherein the cycloalkane is cyclohexane.

8. A process according to claim 1, wherein the reaction is carried out in the presence of a solvent, and the solvent is separated from the reaction mixture.

9. A process according to claim 1, which comprises the following steps (i), (ii), and (iii):
(i) a step for separating the first component containing the cycloalkane, the second component containing the cycloalkanone and the cycloalkanol, and a component containing the oxidizing catalyst, by-produced acid component and a derivative thereof, at which the first component and the second component are separated from each other by distillation;
(ii) a step for separating the cycloalkane from the first component and then recycling the separated cycloalkane to the oxidizing reaction system; and (iii) a step for separating the cycloalkanol from the second component and then recycling the separated cycloalkanol to the oxidizing reaction system.

10. A process according to claim 9, wherein the oxidizing catalyst is separated from the component containing the oxidizing catalyst, the by-produced acid component, and a derivative thereof.

11. A process according to claim 9, wherein the reaction is carried out in the presence of a solvent, the solvent is separated from the reaction mixture, and the separated oxidizing catalyst is recycled to the oxidizing reaction system.

12. A process according to claim 9, wherein by-produced water is separated from the first component, with which water the acid component or a derivative thereof is treated by at least one means selected from extraction, hydrolysis, saponification, and neutralization.

13. A process according to claim 9, wherein a step for supplying the cycloalakne and the catalyst, a step for carrying out the oxidizing reaction, the step (i), the step (ii), and the step (iii) are conducted continuously.

14. A process according to claim 1, wherein the oxidizing catalyst is an imide compound represented by the formula (II):

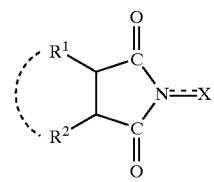

(II)

wherein $R^1$ and $R^2$ are the same or different, each representing a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may be coupled together to form a double bond or an aromatic- or non-aromatic ring; the aromatic- or non-aromatic ring composed of $R^1$ and $R^2$ may have at least one imide unit represented by the aforementioned formula (I); and X has the same meaning as defined above.

15. A process according to claim 1, wherein the oxidizing catalyst is at least one compound selected from the group consisting of N-hydroxysuccinimide,
N-hydroxymaleimide,
N-hydroxyhexahydrophthalimide,
N,N'-dihydroxycyclohexanetetracarboximide,
N-hydroxyphthalimide,
N-hydroxytetrabromophthalimide,
N-hydroxytetrachlorophthalimide,
N-hydroxyhetimide,
N-hydroxyhimimide,
N-hydroxytrimellitimide,
N,N'-dihydroxypyromellitimide, and
N,N'-dihydroxynaphthalenetetracarboximide.

16. A process according to claim 1, wherein the amount of the oxidizing catalyst is 0.001 to 1 mol relative to 1 mol of the cycloalkane.

17. A process according to claim 1, which further employs a co-oxidizing agent.

18. A process according to claim 17, wherein the co-oxidizing agent is a compound containing at least one element selected from the group consisting of Group 3 elements, Group 4 elements, Group 5 elements, Group 6 elements, Group 7 elements, Group 8 elements, Group 9 elements, Group 10 elements, Group 11 elements, and Group 13 elements.

19. A process according to claim 17, wherein the amount of the co-oxidizing agent is 0.001 to 0.7 mol relative to 1 mol of the cycloalkane.

* * * * *